(12) United States Patent
Nace

(10) Patent No.: US 8,308,671 B2
(45) Date of Patent: Nov. 13, 2012

(54) KNEE ORTHOSIS

(76) Inventor: Richard A. Nace, San Jose (CR)

( * ) Notice: Subject to any disclaimer, the term of this patent is extended or adjusted under 35 U.S.C. 154(b) by 1046 days.

(21) Appl. No.: 12/200,394

(22) Filed: Aug. 28, 2008

(65) Prior Publication Data

US 2010/0056970 A1    Mar. 4, 2010

(51) Int. Cl.
*A61F 5/00* (2006.01)
(52) U.S. Cl. .................... 602/26; 602/5; 602/23
(58) Field of Classification Search ............ 602/5, 16, 602/23, 26–29
See application file for complete search history.

(56) References Cited

U.S. PATENT DOCUMENTS

| | | | |
|---|---|---|---|
| 2,587,166 A * | 2/1952 | Jovick .................... 602/26 |
| 4,493,316 A | 1/1985 | Reed et al. |
| 4,856,501 A | 8/1989 | Castillo et al. |
| 4,865,024 A | 9/1989 | Hensley et al. |
| 5,520,622 A | 5/1996 | Bastyr et al. |
| RE37,209 E | 6/2001 | Hensley et al. |
| 6,537,237 B1 | 3/2003 | Hopkins et al. |
| 7,037,287 B2 | 5/2006 | Cormier et al. |
| 7,048,704 B2 | 5/2006 | Sieller et al. |
| 7,198,610 B2 | 4/2007 | Ingimundarson et al. |
| 7,311,687 B2 | 12/2007 | Hoffmeier et al. |
| 7,534,220 B2 | 5/2009 | Cormier et al. |
| 2002/0183674 A1 | 12/2002 | Castillo |
| 2007/0066923 A1 | 3/2007 | Sreeramagiri |

FOREIGN PATENT DOCUMENTS

WO    2007109112 A3    9/2007

* cited by examiner

*Primary Examiner* — Kim M Lewis
(74) *Attorney, Agent, or Firm* — Larson & Larson, P.A.; Frank Liebenow; Justin P. Miller

(57) ABSTRACT

A knee orthosis device provides medial, lateral, and rotational control of a knee joint. The novel knee orthosis device stabilizes an injured or surgically repaired, or a weakened knee joint having a neurological disability, which causes instability therein, by applying adjustable corrective and therapeutic forces, which operate to stabilize and protect the knee as well as to correct abnormal gait and to rehabilitate the knee joint and surrounding muscles above and below the knee by encouraging and recruiting said muscles to operate again more normally through the use of a dynamic swing assist mechanism. The knee orthosis also provides dynamically conformable thigh and shin cuff circumferential band systems in combination with a multitude of other elements that conform to the constant dimensional changes of the muscle groups that are surrounded by the knee orthosis device during ambulatory or athletic motion.

10 Claims, 7 Drawing Sheets

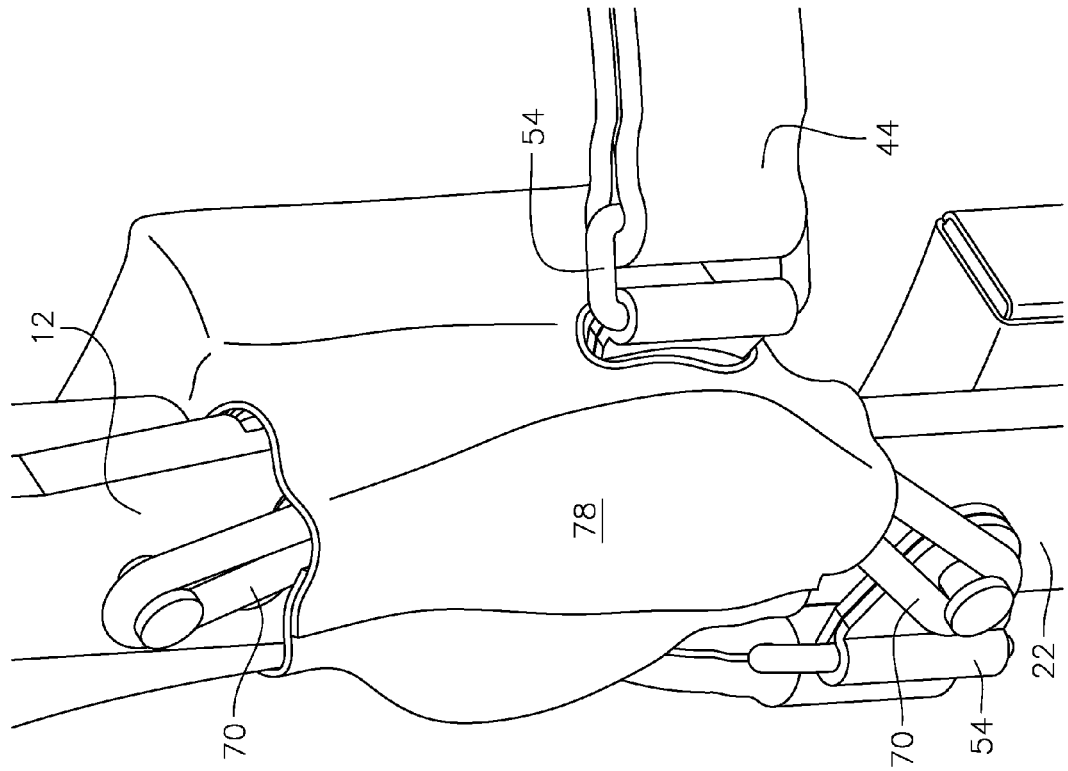
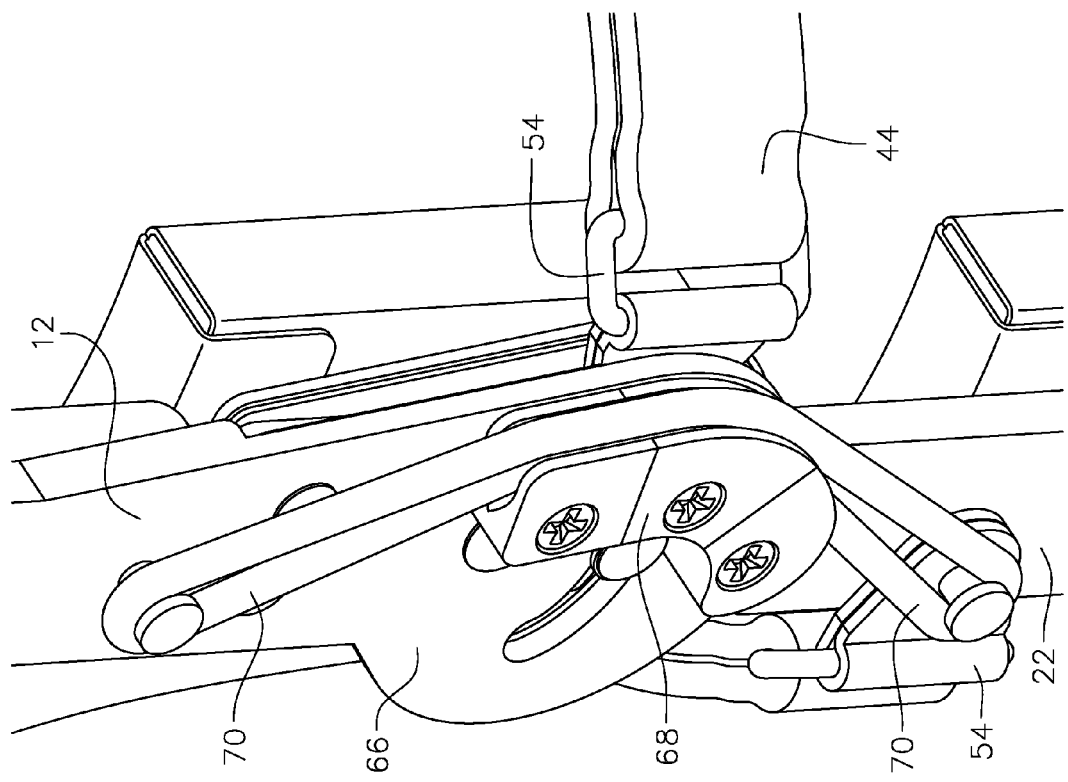

KNEE ORTHOSIS

FIELD OF THE INVENTION

The present invention relates to a knee orthosis device used to provide medial, lateral, and rotational control of a knee joint. More particularly, it relates to a knee orthosis device used for stabilizing an injured or surgically repaired, or a weakened knee joint having a neurological disability, which causes instability therein, by applying adjustable corrective and therapeutic forces, which operate to stabilize and protect the knee as well as to correct abnormal gait and to rehabilitate the knee joint and surrounding muscles above and below the knee by encouraging and recruiting said muscles to operate again more normally.

BACKGROUND OF THE INVENTION

Orthotic devices and appliances commonly referred to as "orthotics," are known in the prior art and have been utilized for many years by orthotists (a maker and fitter of orthotics), physical therapists, and occupational therapists to protect an injured or surgically repaired knee joint, or a weakened one caused by a neurological disability. Knee orthotics are also used to assist in the rehabilitation of a patient's knee joint and the associated limbs or adjacent skeletal parts of the patient's body related to knee instability.

Webster's New College Dictionary defines "orthotics" as a branch of mechanical medical science that deals with the support and bracing of weak or ineffective joints or muscles. The word "ortho" actually comes from Greek and means "to straighten." Orthotics are used to support and straighten the effected joint and assist to correct normal human function as closely as possible. Orthotics used as limb braces have typically been designed to support and protect the joint that is associated with knee injury or post surgical use, and for alleviating pain associated with joint movement at the particular location being treated.

Knee laxity, due to ligament injury, can cause significant instability to the knee joint thereby predisposing the joint to further instability and more serious injury. The medial collateral ligament (MCL) and lateral collateral ligament (LCL) provide side to side stability of the knee joint. Injury to the MCL or LCL can result in lateral instability of the knee.

The anterior cruciate ligament (ACL) is responsible for controlling the forward glide of the tibia in relation to the femur. This movement is called "anterior tibial translation." The ACL, in combination with the other ligaments, of a healthy knee joint restrict the rotation or twisting of the knee. Injury to the ACL can result in rotational and anterior instability of the knee.

The posterior cruciate ligament (PCL) is the primary restraint to post translation of the tibia on the femur and acts as a secondary restraint to varus/valgus movements and external rotation. Injury to the PCL can result in posterior instability of the knee whereby the patient feels that the knee can "pop-out" of place. PCL injuries are the least common form of knee instability injury.

An injury or tear of any one of the aforementioned ligament predisposes the knee joint to secondary injuries to the other ligaments, as well as to the meniscus and articular cartilage of the knee. Approximately 50% of all ACL injuries occur in combination with damage to the meniscus, articular cartilage or other ligaments. Protecting and supporting a weakened knee joint after injury or pre or post-operatively, from the medial, lateral or rotational forces exerted upon the knee during walking, squatting and other movements is the primary purpose of a knee orthosis device for knee instability.

Patients who have suffered a traumatic brain injury, stroke or who have Cerebral Palsy, MS or other neurological disabilities that results in muscle weakness, a loss of proprioception and poor balance may also require a knee orthosis to protect and stabilize the knee joint from injury and to allow for safe ambulation.

It is also known that ligaments become more compliant with age, which can also lead to significant knee laxity. Knee laxity may be broadly defined as abnormal displacement or rotation of the tibia with respect to the femur. In the unloaded state, knee stability is provided by the ligaments, joint capsule and other soft tissues. In the loaded state, the interactions between ligaments, other soft tissues, condylar geometry, and tibiofemoral contact forces generated by muscle activity and gravitational forces maintain knee stability. Joint laxity reflects an impairment of the passive restraint system for which muscle activity may or may not compensate. Knee joint laxity may adversely affect joint mechanics which can lead to an unstable knee joint and abnormalities in gait kinetics.

Knee instability, whether due to ligament injury, surgery or muscle weakness in the muscles supporting the knee joint during locomotion and other activities may require a supportive and protective knee orthosis device to prevent secondary damage to the knee resulting in more serious injury. A knee orthosis device used to treat knee instability must provide medial, lateral and rotational support of the knee during walking and other activities to adequately support and protect the knee joint.

The prior art includes a multiplicity of various knee brace designs. However, most knee instability brace designs include a rigid anterior thigh cuff, a rigid anterior shin cuff, a rigid medial upright with a unicentric or polycentric hinge, a lateral upright with a unicentric or polycentric hinge, a strapping system, and condyle pads or another stabilizing force system at mid knee joint on both sides. Examples of such devices can be seen in U.S. Pat. No. 4,493,316 to Reed et al., U.S. Pat. No. 4,856,501 to Castillo et al., US Published Application No. 2002/0183674 to Castillo and US Published Application No. 2007/0066923 to Sreeramagiri. Other knee instability or ligament braces have a rigid anterior thigh cuff, a rigid posterior calf cuff, rigid medial and lateral uprights, condyle pads, a strapping system and unicentric or polycentric hinges such as the "Donjoy Defiance" brace. Still other knee instability knee braces have a rigid posterior thigh cuff, a rigid anterior shin cuff, rigid medial and lateral uprights with polycentric hinges, condyle pads and a strapping system such as the "Donjoy 4Titude" brace.

Therefore, what is clearly seen in the prior art of all knee laxity or ligament braces are rigid structures having a top structure of the brace constructed as one uniform part (thigh cuff and upper portion of the upright), which then connects at the hinge to the lower rigid structure of the brace (lower uprights and shin or calf cuff). These rigid structures, which typically employ static straps, may immobilize the knee joint. However, they lack the ability to flex and conform to the motions of a patient's muscular areas around the knee joint when the patient is walking, squatting or rising from a sitting position, let alone exerting a more rigorous motion such as running, dancing or performing any other motion required from someone engaged in a sport activity. Simply put, the prior art braces lack any "dynamic conformability." In other words, the prior art braces and their static straps do not conform to the ever changing, and often unpredictable, dynamics of the knee joint and the surrounding muscles there around.

The static nature of the strapping seen in the prior art not only prohibits, but discourages expansion, which then would permit a return to a relaxed state after the strap is "unloaded." That is because all current prior art braces that employ static strapping use such strapping to hold the brace in place and to mitigate brace migration. And for these reasons, the prior art knee laxity and/or ligament braces are inadequate and are in great need of improvement.

Another troubling problem with the rigid structure of existing knee instability brace designs is that the braces can alter normal gait biomechanics. Because they are rigid in design, and because of the dynamic motion of the knee and leg when walking, squatting, running, etc., the braces are prone to slippage and brace migration. Simply put, the prior art braces do not conform to the constantly changing shape of the leg above and below the knee joint during motion. Further, the greater the intensity of the body motion, the more likely brace slippage and migration will occur.

The most recent knee ligament brace innovations involve condyle pad construction or strapping systems intended to keep the brace in place during normal activities. These new components have been added to the rigid structure of the brace (uprights and cuffs). Such "improvements" can be seen in U.S. Pat. No. 7,198,610 to Ingimundarson, et al. and PCT Application Publication No. WO 2007/109112, also to Ingimundarson, et al. In spite of these innovations and supposed improvements, brace migration continues to be one of the most common complaints among brace users.

Brace migration during brace use can be extremely problematic for the patient. If the condyle pads, which are also static in the prior art, become misaligned, optimal brace protection of the knee joint is compromised. As the brace slips down, the axis of the brace and the axis of the knee joint will not align correctly, and this can place unwanted forces on the knee joint, which affect gait and the normal biomechanics of walking and other activities. Patients can become noncompliant and will thus avoid wearing their brace because it is extremely inconvenient to constantly readjust the brace during certain activities. A brace that is designed and engineered to not slip or migrate with significant activity would be a significant improvement over existing knee instability braces and is a feature that is clearly needed in knee orthosis devices.

Further, many of the existing knee braces utilize range of motion stops (flexion and/or extension) that must be manually inserted into the hinge assembly with tools to set the desired degrees of flexion and extension limits prescribed by the physician. This continues to be a problem, which clearly needs improvement thereupon.

In addition, no knee instability or knee ligament braces, which are currently available, are designed to maintain or strengthen the musculature of the leg, post injury or post surgery and during brace use. Due to the fact that the gait of a patient having significant knee laxity or a knee ligament injury is usually altered as a means to avoid pain and re-injury of the knee joint, and further that known prior art rigid knee braces contribute to an abnormal and altered gait, full use of the leg muscles is significantly reduced, which then leads to significant muscle atrophy. It is non uncommon for a patient who suffers a knee ligament injury to lose muscle mass in the thigh area of the leg in as little as eight to fourteen days of limited activity. Often, measurable loss of thigh circumference, a common means for measuring the loss of muscle mass, can be one to three inches of thigh circumference.

The present invention is uniquely designed to correct for alterations in gait by providing significant knee support, correcting knee joint alignment, and through the use of a dynamic swing assist, maintain an as normal as possible heel to toe walking pattern. Normal heel to toe walking is critical to initiate the firing of all of the muscles in the quadriceps in the correct firing pattern, which is necessary to maintain normal muscle mass and muscle strength. By correcting abnormal gait patterns and facilitating a heel to toe walking pattern, the present and novel invention provides rehabilitative benefits to the patient that are not available with existing prior art knee ligament braces. By correcting gait and facilitating a heel to toe walking pattern, muscle use is maintained, thereby diminishing the potential for the loss of muscle mass and strength. This is a significant benefit over other knee ligament braces of the prior art, as it can lead to significant reduction in the rehabilitation necessary to re-strengthen the leg musculature post injury or surgery.

What is therefore needed is a complete knee laxity brace that can protect and support the knee medially, laterally and rotationally, provide a swing-assist function for extension, provide a corrective and therapeutic force that can return the patient to a more true normal gait (heel-to-toe strike while walking) to prevent abnormal rotation of the knee joint, all the while recruiting atrophied muscles to work again and to rehabilitate themselves so that the patient can once again return to the closest possible "normal" condition based upon the specific progression of their respective knee laxity condition. The goal for any advancement in the art should be an improvement from "abnormal gait" to a more biomechanically correct normal gait kinetic, believed to be a significant factor in reducing the rehabilitation necessary to allow for unaided ambulation. A truly rehabilitative knee brace would maintain muscle strength or strengthen the leg musculature over time using dynamic adjustable components such that a reduction of pain and rehabilitation time would be both evident and realized. Such a described and needed brace currently does not exist in anywhere in the prior art. Simply put, an improved knee laxity or ligament brace should be used with patients who can begin "brace therapy" immediately after injury, at the time before a surgical procedure is be performed on the knee joint and immediately post surgery to effectively improve the condition of the knee joint with routine brace use while providing support and protection of the joint.

SUMMARY OF THE INVENTION

The present invention provides superior medial, lateral, and rotational support to the knee. A system of air bladders situated at mid-knee and below the knee can be inflated to provide the optimal brace support and protection of the knee joint in all planes for significant varied physical activities. At the same time, the present invention better facilitates a more normal gait with use of the brace through the means of an adjustable dynamic swing assist incorporated into the brace design when compared to the prior art.

The design of the new device includes a double upright design with a flexible posterior thigh cuff and a flexible anterior shin cuff with rigid uprights on both the medial and lateral side of the knee joint. An elastic anterior proximal thigh strap, an elastic distal posterior calf strap, static anterior thigh strap positioned between the proximal anterior elastic thigh strap and the patella, and a bioengineered semi-static calf strap located mid-way between the distal posterior calf strap and the crease of the knee joint provide bands of support encasing the rigid uprights above and below the knee joint. All of the straps are attached to the uprights with pivoting D rings which allow the straps to conform to changes in shape and angle of the leg during varied activities. A fifth adjustable static strap can be located on the anterior side of the leg just below the patella to provide an anterior lever arm to prevent forward tibial movement that is often seen with significant ACL injury or ACL ligament laxity.

A medial and lateral unicentric or polycentric hinge at the knee joint on each upright is aligned to allow normal flexion and extension movement of the knee. A flexion and extension range of motion control on one or both hinges allows the fitter to quickly and easily limit the motion of the knee to a specific range of flexion or extension that allows for safe flexion and extension of the knee.

Each of the four bands of circumferential support for the medial and lateral uprights is bio-engineered to conform to the specific change in dimensions of that part of the leg, which will occur when walking, running, sitting to stand or standing to sit as well as all other related activities. Each band will morph or change its shape with the natural change in dimension of that part of the leg with multiple variations of normal movement during different activities. This unique feature of the present invention allows for superior brace conformity with the leg during locomotion and the various leg movements associated with other activities (i.e., walking, running, playing golf, playing tennis, squatting, sit to stand, etc.).

To achieve this unique feature of brace conformance to the changing leg shape and angle in the present brace design, the leg was studied on people of different stature (tall, short, thin, obese, etc.) during different common activities. What was discovered was that as the human leg moves into flexion, the flexor muscles on the back of the leg contract and change shape becoming larger in circumference at mid-muscle to create the flexing motion of the leg. As the flexor muscles contract, the extensor muscles on the front of the leg elongate along the leg thereby decreasing in circumference as these muscles relax and stretch out. As the human leg moves from a flexed position to extension with activation of the extensor muscles during leg extension (squat to stand), the extensor muscles on the front of the leg increase in circumference at the muscle belly (located at approximately mid muscle), and the flexor muscles on the back of the leg relax and lengthen.

At rest, leg girth and muscle mass are usually smaller on the distal end of the leg (i.e., the calf). Circumference of the leg tends to increase significantly from mid knee joint to mid thigh, and then increase in size more slowly becoming more consistent circumferentially up to the hip. The change in angle of the upper posterior leg compared to the mid-line of the body is relatively greater as you measure from the knee joint up to the mid-thigh area.

Most importantly, the change in the circumference at a given cross section of the upper leg will change its shape and size depending on the movement at any place in time with normal locomotion. The variance in the angle of the muscle compared to the mid-line of the leg at any point in time will also vary significantly. The same change in circumference at any cross-section of the calf muscle of the leg and the angle of the calf muscle during different stages of flexion and extension will also vary considerably.

To provide maximum conformity to the leg at any cross-section of the leg, to which a knee brace may attach, during a multitude of leg motion possibilities, a pivoting flexible band employed around the leg is required. The brace must be capable of changing its circumference as well as accommodating variations in muscle angle at any specific braced cross section of the leg. Since leg circumference and muscle angle will vary depending on the specific location of the cross sectional band around the leg, four circumferential bands, two located between the knee joint and approximately mid-thigh and two located between the knee joint and approximately mid-calf would each have to be constructed with different properties of conformance, flexibility, and support relative to one another. By combining variations in plastics with differing coefficients of stiffness and width affixed at differing angles on one side of the leg, and by using strapping materials with differences in elastic properties, which may be combined with pads to provide specific points of leverage on the other side of the leg with pivoting rivet attachments, allows the brace to morph or change with natural changes in the leg with movement to accommodate that movement to prevent brace migration or slipping. This is a major improvement over the prior art.

Maintaining as normal a gait as possible, post injury or post surgically, is extremely important in maintaining both muscle strength and muscle memory. If the patient favors that injured leg to avoid pain, an abnormal gait will develop. Although the abnormalities in gait can vary depending on the specific injury and severity of the injury, the patient compensates the way they walk to avoid pain and discomfort on the affected leg. Usual accommodations in gait include changes in movement at the hip (reduced hip flexion, hip abduction), knee (reduced knee flexion) and ankle/foot (loss of normal heel to toe transition from initial weight bearing to toe off). A loss of knee power and ankle power also may be significant, resulting in an altered gait and a reduction in step length.

Disuse of full gait kinetics results in both loss of muscle mass and muscle strength as well as a potential change in muscle memory. Loss of muscle strength post injury or post surgery can require significant rehabilitation. For example, standard rehabilitation from an ACL surgery is anticipated to be 40 to 50 weeks. If a knee brace can maintain a more normal gait, recruiting all of the muscles used in normal ambulation, less muscle atrophy and loss of muscle mass and strength should occur, leading to a decrease in the time necessary for full rehabilitation. This has significant benefits to the patient and is another feature of the present invention, which is a major improvement over the prior art.

Changes in muscle memory resulting from thousands of repetitions of an abnormal gait post injury or post surgery will potentially override the programmed muscle memory of a normal gait. This occurs neurologically. Through thousands of repetitions of walking normally, the leg muscles store the precise sequence of muscle firing to result in a normal gait. These patterns of muscle firing are stored in the spinal cord and are referred to Central Program Generators (or CPG's). Walking naturally becomes a reflex activity that is programmed neurologically so that once learned, the specific muscle firing pattern for walking becomes a learned activity with the muscle firing pattern for all of the muscles involved stored as a CPG. If a chronic injury results in a significant change in walking, muscle firing patterns change as movement or gait patterns change. If repeated for a significant period of time, the CPG associated with normal gait becomes altered and can be replaced with an abnormal gait pattern. Preventing or reducing changes in normal walking kinetics has significant benefits in reducing the rehabilitation necessary to restore a normal walking CPG post injury or surgery and is yet another feature of the present invention and yet another major improvement over the prior art.

The design of the present knee brace addresses the importance of maintaining muscle firing of all muscles used during normal gait, which has hereto be considered let incorporated into a knee brace or orthosis device. The adjustable dynamic swing assist of the present invention helps to maintain a more normal gait. Heel strike with gait is important in that it is necessary to fire all of the quadriceps muscles. The adjustable dynamic swing assist is designed to facilitate heel strike during ambulation when wearing the brace.

The present invention provides a knee instability or knee ligament support knee orthosis (or "knee brace") easily fabricated in a wide range of sizes for either the left or right knee to treat instabilities caused by injury or surgery to the ligaments of the knee, meniscus, articular cartilage or a combination of injury of the knee joint. Such a novel brace of the present invention provides easily managed controls for setting the desired degree of flexion and extension. The knee orthosis of this invention will support and protect the medial, lateral sides of the knee as well as supporting and protecting the rotational movement of the knee during ambulation and other activities, improve knee joint alignment, and all the while be adjustable as the condition of the knee improves or deteriorates to provide the necessary support and protection of the damaged knee joint and thereby improve knee joint mechanics during gait.

With knee instability or a knee laxity condition, the knee orthosis of the present invention provides medial, lateral, and rotational support of the knee as well as providing controlled flexion and extension, which is continually maintained, all the while providing joint rehabilitation by initiating a more normal firing of the quadriceps muscles thereby correcting abnormal gait.

The current invention in one embodiment achieves this significant improvement with an adjustable dynamic fulcrum, positioned on the lateral side of the degenerated knee joint, to allow the clinician to quickly and easily adjust the brace to provide the necessary gait swing assist, which then facilitates a more normal gait for the overall knee, as needed during any knee rehabilitation process.

The present invention accomplishes the desired result of corrective ambulatory support by utilizing a polycentric hinge on the lateral side of the brace and a uni-centric hinge component on the medial side of the brace. A semi-rigid cuff is circumscribable about the front of the lower leg. The lower member of each hinge is attached to a lateral and medial upright element integrally attached to the semi-rigid cuff. A semi-rigid, dynamic conformable thigh cuff is aligned with the back of a patient's thigh, above the knee joint. The thigh cuff has a lateral and medial element extending downwardly to engage a top hinge arm of each hinge. A spring or elastic banded adjustable fulcrum polycentric hinge component is used to assist leg extension-flexion during walking, squatting and sitting. By repositioning a plurality of setting blocks, different degrees of tension can be introduced into the polycentric hinge element. The adjustable fulcrum is a rehabilitative mechanism for the leg musculature that assists in the supporting and surrounding of the knee joint area.

In a preferred embodiment, the knee instability brace of the present invention provides a system for applying a corrective and therapeutic force to the knee joint area to assist in the traditional functions of a knee instability or ligament brace but with the added benefit of actually correcting gait kinetics and preventing abnormal rotation of the knee joint. Therefore, with such a system, a patient with knee instability will realize a significant reduction or elimination of hip abduction, a significant support medially, laterally and rotationally at the knee joint area, a transformation from an abnormal lateral, medial, or flat foot placement walk to a near normal heel-to-toe foot placement and a lengthening of their actual step.

This is all accomplished by a novel system that incorporates precisely placed, but adjustable, inflatable or pneumatic bladders, or formed cushions, which apply optimal corrective force in all planes above and below the knee joint, and on both sides thereof, to truly balance and support the knee joint and reduce unwanted and potentially harmful movements, medially, laterally and rotationally during ambulation and other related activities. The corrective force system of the novel present invention physically limits the available movement of the knee joint within a protected range that will allow normal activities while restricting movement within a restricted range to protect the ligaments and other structures of the knee joint. The system allows for the patient to fine tune the support of the knee brace by adjusting the corrective force elements since the patient knows what truly hurts, what does not hurt and what a comfortable gait feels like for them.

In addition, the present invention significantly restricts abnormal rotation of the knee, which then also protects the knee joint from instability due to the underlying cause of the knee joint laxity from further damage to the knee joint. This is realized by a plurality of contoured air bladders, which, when inflated, will limit the motion of the knee within a protected range. The corrective force system also contributes to the reduction or elimination of the abnormal rotation of the knee. An adjustable anterior tibial strap located below the patella will prevent forward slipping of the tibia in relation to the femur often seen with ACL injuries. These combined innovations in the present invention result in a significant rehabilitation of the knee joint and leg musculature to support and protect the knee during ambulation and other activities.

Still further, to assist with the comfort level of the brace on the patient and to avoid the brace from slipping or moving when employed, a material having a high coefficient of friction, but which does not cause discomfort against the skin of the patient, is employed along the surfaces of material wraps that surround the hinges and which come in contact with patient's skin.

Still even further, the proximal thigh cuff circumferential support band consisting of an angled flexible thigh cuff permanently attached to the upper end of the uprights and an elastic strapping system attached to pivoting D rings on both upper ends of the uprights provides a dynamic band of support at the thigh, which conforms to the ever changing shape and angular dynamic motion of the leg during ambulation, running, and a myriad of other activities, all the while maintaining its position on the leg. A preferred angle for the flexible thigh cuff is 15-20 degrees.

A second upper anterior thigh strap placed between the proximal thigh strap band and the patella is a static strap with a pressure leverage pad located at mid strap attached to the uprights with pivoting D rings located at a point on the extensor muscles of the thigh with minimal changes in shape or angle with walking and other activities which acts in combination with the thigh circumferential flexible support band to provide added stability to the upper leg circumferential support mechanism of the brace.

A semi-static strap is located behind the knee below the crease in the knee as to not enter into the crease of the knee with extreme flexion motion (squatting) and above mid calf to accommodate the changes in shape and angles of the lower leg at this specific location with sitting, standing, walking, running, and other activities such that the strap will expand, contract, and change angle to morph the shape of the lag with a plurality of movements without slipping or migration.

The distal calf cuff circumferential support band consisting of the angled flexible shin cuff permanently attached to the lower end of the uprights and an elastic strapping system attached to pivoting D rings on both lower ends of the uprights provides a circumferential supportive band of support at the calf approximately 4 inches below mid patella that conforms to the changing shape and angular dynamic motion of the leg with sitting, standing, ambulation, running, and a myriad of other activities while maintaining its position on the leg.

The combined anterior upper thigh cuff flexible supportive circumferential band, anterior static pivoting thigh strap, semi-static posterior below knee crease strap, and lower posterior flexible calf supportive circumferential band all provide enhanced brace support and stability with superior anti-migration properties to support the rigid double uprights by conforming to the unique changes, shape and angles in the leg with ambulation or other movement of the leg when walking, running, and other more complex activities. Improved stability of the brace (no to minimal migration) derived from this unique and innovative circumferential support system above and below the knee provides a significant improvement over the prior art in knee instability braces designed to provide significant support and protection of the knee joint.

It should be noted that known Neoprene "slip on" or "knee wrap" braces, such as that seen in U.S. Pat. No. 4,064,874 to Valin are conforming and can change with the changes in the shape of the leg with motion, but do not have the rigid support necessary for more significant knee ligament injury or laxity and do not provide the rotational support necessary for ligament injury or post surgery rehabilitation.

Still even further, the pre-operative, post-operative brace of the present invention utilizes the unique combination of features described above with a flexion-extension control mechanism that is incorporated into the brace permanently, which can be set in 1° steps to allow precise range of motion limits, which then allows for a single patient to use the same brace before and after surgery, in those cases that require surgery.

The knee orthosis of the present invention having an adjustable dynamic swing assist is especially and uniquely designed to provide for a corrective gait, knee support, knee protection, knee stabilization, patient proprioceptive input and improved knee balance control needed for patients who suffer from neurological deficits in the lower extremity. Knee instability is prevalent in many patients who develop significant abnormalities from abnormal gait due to the neurological deficits, muscle weakness and knee instability. The muscle memory for normal gait has been disrupted and a gait corrective and muscle rehabilitative knee brace in addition to a supportive brace is indicated for rehabilitation for these patients. Such can found in the knee orthosis of the present invention.

BRIEF DESCRIPTION OF THE DRAWINGS

This invention can be best understood by those having ordinary skill in the art by reference to the following detailed description, when considered in conjunction with the accompanying drawings in which:

FIG. 8 is a close-up view of one of a hinged element employed with the knee orthosis of the present invention when a wrap enclosure has been removed around said hinged element; and FIG. 9 is close-up view of one of a hinged element employed with the knee orthosis of the present invention when the wrap enclosure surrounds said hinged element.

DETAILED DESCRIPTION OF THE INVENTION

Figure 1:
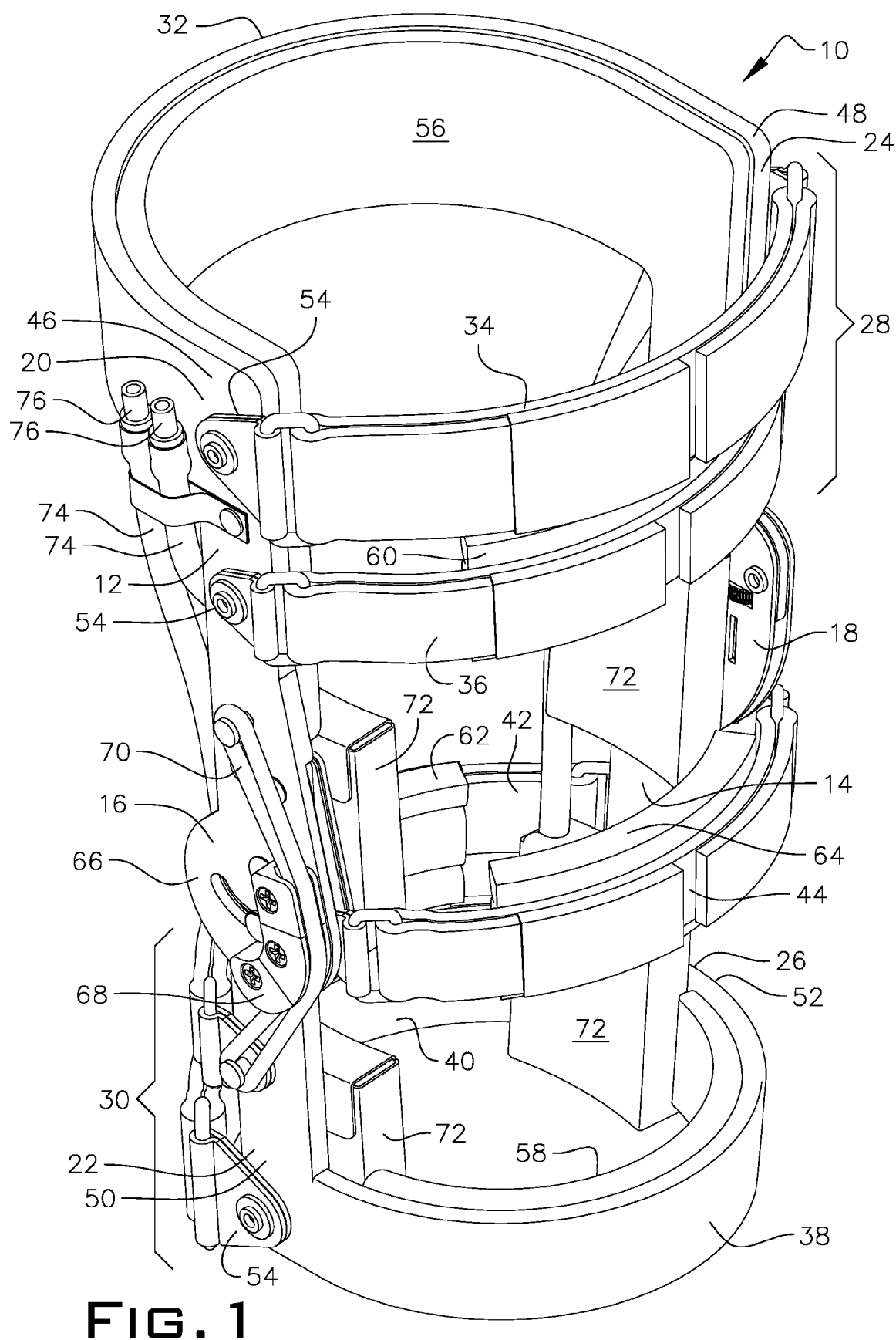
FIG. 1 is a perspective view of a novel knee orthosis of the present invention in an elongated state.

Throughout the following detailed description the same reference numerals refer to the same elements in all figures.

Referring to FIG. 1, a novel knee orthosis 10 of the present invention is shown, and hereinafter described, for use with a patient with a knee injury or for employment on leg of patient before or after surgery. It is important to note immediately that the novel knee orthosis 10 of the present invention can be used on the same patient before and after a surgical procedure to replace or repair an injured or diseased knee joint. No knee orthosis or brace hereto before has ever contemplated, let alone be employed, the use of the same orthotic device for pre and post-surgery. Therefore, knee orthosis 10 has all of the advantages as set forth above in the Summary of the Invention and improves upon and fixes all of the deficiencies as also described above, but generally discussed in the Background of the Art.

Knee orthosis 10, in a preferred embodiment, employs a pair of opposed first and second vertical struts 12 and 14 as shown in FIG. 1. However, nothing herein limits knee orthosis 10 from employing a single strut design, although not shown in the figures. First and second vertical strut, 12 and 14, each employ a hinged element. As shown herein, first vertical strut 12 employs a polycentric hinge 16 where as second vertical strut 14 employs a unicentric hinge 18. However, nothing herein limits the present invention to this specific preferred embodiment, as alternate embodiments reverse the shown hinges 16 and 18 to the other opposing strut and further alternate embodiments employ a pair of polycentric hinges 16 or a pair of unicentric hinges 18 on both struts 12 and 14.

Polycentric hinged 16, as shown in FIG. 1, is intermediately disposed top and bottom portions 20 and 22 of first vertical strut 12, whereas unicentric hinge 18 is intermediately disposed top and bottom portions 24 and 26 of second vertical strut 14. In the preferred embodiment, the two hinges are axially aligned along a traverse plane of the patient. However, in alternate embodiments of knee orthosis 10, the axes of the two hinges are slightly off-set.

With continuing reference to FIG. 1, it is shown that knee orthosis 10 includes a dynamically conformable thigh circumferential band system 28 and a dynamically conformable shin circumferential band system 30. Thigh circumferential band system 28 includes a thigh cuff 32, a first thigh strap member 34 and second thigh strap member 36. Shin circumferential band system 30 includes a shin cuff 38, a first shin strap member 40 and second shin strap member 42. In the preferred embodiment, as shown in FIG. 1, thigh cuff 32 is disposed along a posterior side of a thigh muscle group area of a patient when knee orthosis 10 is employed to a patient's leg. As further shown, first and second thigh strap members, 34 and 36 are disposed along an anterior side of the thigh muscle group area of the patient when knee orthosis 10 is employed to the patient's leg. Further, as to the preferred embodiment, and as shown in FIG. 1, shin cuff 38 is disposed along an anterior side of a shin/calf muscle group area of a patient when knee orthosis 10 is employed to a patient's leg. And, first and second shin strap members, 40 and 42 are disposed along a posterior side of the shin/calf muscle group area of the patient when knee orthosis 10 is employed to the patient's leg.

With continuing reference to FIG. 1, knee orthosis also employs a tibia or patella strap 44 across the anterior side of a knee joint and generally disposed over below the "knee cap" of the patient.

Nothing herein limits knee orthosis 10 to the posterior and anterior positioning of the various elements of both the dynamically conformable thigh and shin circumferential band systems 28 and 30. What has been described so far and what is further illustrated in FIG. 1 is merely the preferred embodiment. Alternate embodiments of the present invention reverse the positioning of both the dynamically conformable thigh and shin circumferential band systems 28 and 30.

However, with further reference to the preferred embodiment of knee orthosis 10, as shown in FIG. 1, thigh cuff 32 surrounds a portion of a circumference of the thigh muscle group, by which first thigh strap member 34 completes said circumference. Second thigh strap member 36 is positioned below first thigh strap member 34 along the anterior side of the patient's thigh muscle group. The dynamically conformable thigh circumferential band system 28 is also considered to be located at an upper section of knee orthosis 10, which is the section that realizes or experiences the greatest amount of dynamic conformability during ambulatory or athletic movement of the patient's leg. Also, in the preferred embodiment, thigh cuff 32 is slightly angled upwards on one side by 15 to 20 degrees. Some alternate embodiments provide for a greater degree of angling while others provide for no angling of thigh cuff 32.

With continuing reference to the preferred embodiment of knee orthosis 10, as shown in FIG. 1, shin cuff 38 surrounds a portion of a circumference of the shin/calf muscle group, by which first shin strap member 40 completes said circumference. Second shin strap member 42 is positioned above first shin strap member 4o along the posterior side of the patient's shin/calf muscle group. The dynamically conformable shin circumferential band system 30 is also considered to be located at a lower section of knee orthosis 10, which is the section that realizes or experiences the second greatest amount of dynamic conformability during ambulatory or athletic movement of the patient's leg, when compared to the upper section of knee orthosis 10.

Again, with reference to FIG. 1, it is shown that opposing ends of thigh cuff 32 are attached to upper end portions, 46 and 48, of first and second vertical struts 12 and 14, respectively. In an alternate embodiment, the opposing ends of thigh cuff 32 are integral with first and second vertical strut upper end portions, 46 and 48. Further, as to the preferred embodiment, opposing ends of both first and second thigh strap members, 34 and 36, are also attached to first and second vertical strut upper end portions, 46 and 48. In the preferred embodiment, first and second thigh strap members, 34 and 36, are secured by an attachment element 54 that is pivotable about an axis, which is also its attachment point, such as with D-rings (see FIGS. 5 and 6). Alternate embodiments however employ other types of attachment elements that lend themselves to the dynamic conformable nature of knee orthosis 10.

Further to FIG. 1, it is shown that opposing ends of shin cuff 38 are attached to lower end portions, 50 and 52, of first and second vertical struts 12 and 14, respectively. In an alternate embodiment, the opposing ends of shin cuff 38 are integral with first and second vertical strut lower end portions, 50 and 52. Further, as to the preferred embodiment, opposing ends of both first and second shin strap members, 40 and 42, are also attached to first and second vertical strut lower end portions, 50 and 52. In the preferred embodiment, first and second shin strap members, 40 and 42, are secured by attachment elements 54 that are again pivotable about an axis, which is also its attachment point, such as with D-rings. Alternate embodiments however employ other types of attachment elements that again lend themselves to the dynamic conformable nature of knee orthosis 10.

With reference still to FIG. 1, it is shown that thigh cuff 32 employs a thigh comfort pad 56 along an inner surface of thigh cuff 32 and generally has the same shape thereof. Thigh comfort pad 56 is attached by any well known attachment mechanisms, such as hook and loop material. Further, shin cuff 38 employs a shin comfort pad 58 along an inner surface of shin cuff 38 and generally has the same shape thereof. Shin comfort pad 58 is also attached by any well known attachment mechanisms, such as hook and loop material. Although a multiplicity of different materials can be used within each comfort pad, 56 and 58, in the preferred embodiment foam is employed. However, other materials include gels, liquids and pliable plastics.

As further shown in FIG. 1, additional comfort pads are employed with knee orthosis 10. In particular, second thigh strap member 36 employs comfort pad 60, second shin strap member 42 employs comfort pad 62 and patella or tibia strap 44 employs comfort pad 64. Each comfort pad, 60, 62 and 64 are all mounted along inside strap surfaces of each respective strap. Although a plurality of attachment options exist and can be used with knee orthosis 10, in the preferred embodiment, hook and loop material is employed and allows for comfort pads 60, 62 and 64 to be adjusted and positioned based upon knee orthosis 10 user, patient therapist or doctor. Further, although a multiplicity of different materials can be used within each comfort pad, 60, 62 and 64, in the preferred embodiment foam is employed. However, other materials include gels, liquids and pliable plastics.

Figure 2:
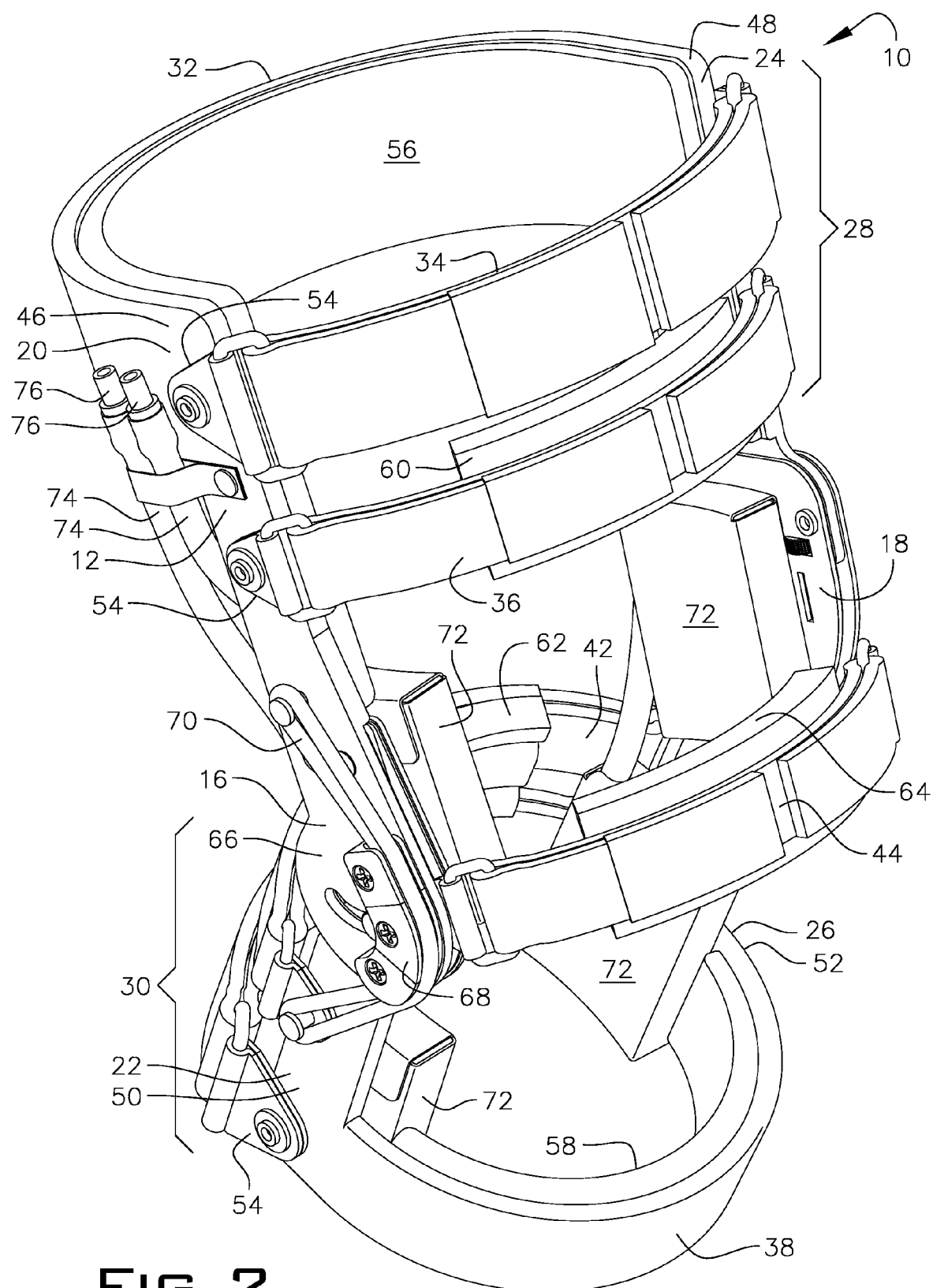
FIG. 2 is a perspective view of the novel knee orthosis of the present invention in a flexed state.

With reference now to FIGS. 1, 2 and 8, it is shown that knee orthosis 10 employs an adjustable gait kinetic swing-assistance mechanism 66, which provides varying tension swing-assist forces to the lower leg portion below the knee joint for correcting abnormal gait (i.e., assists the patient to walk with a proper heel to toe strike gait) and at the same time helps to recruit all of the muscles of the thigh muscle group to "fire" and work and thereby strengthen and rehabilitate themselves. In the preferred embodiment, as shown in FIGS. 1, 2 and 8, the adjustable gait kinetic swing-assistance mechanism 66, is a fulcrum employing a plurality of adjustable setting blocks 68 over which an elastic band 70 is stretched. Setting blocks 68 can be moved and removed to provide a varying amount of tension forces, depending on the needs of the patient. Likewise, different bands 70 having different degrees of elasticity can also be employed and interchanged to again satisfy a very precise and particular need of the patient. With an understanding of these two adjustable elements of the adjustable gait kinetic swing-assistance mechanism 66, it can now be appreciated as to the large number of varying tension forces that can be used with knee orthosis 10 of the present invention.

With even more particularity, setting blocks 68 are mounted in holes (not shown) in mechanism 66, which permits removal and moving thereof. Further, although it is shown that adjustable gait kinetic swing-assistance mechanism 66 is mounted to polycentric hinge 16, nothing herein limits it use to just that one hinge. Further, nothing herein limits the exact placement of adjustable gait kinetic swing-assistance mechanism 66 on an outer surface of a hinged element. In fact, alternate embodiments have adjustable gait kinetic swing-assistance mechanism 66 mounted as integral part of a hinged element or on an inner surface thereof. Still further, nothing limits adjustable gait kinetic swing-assistance mechanism 66 to a fulcrum. Other mechanisms that are used in alternate embodiments include a variably settable cam system and an interchangeable spring element. Still even further, when an elastic band 70 is used, for instance with the fulcrum, nothing herein limits the substitution of a spring element in place of the elastic band 70.

Although not shown in their entirety, both flexion and extension stop elements are employed on at least one the hinged elements, and in the preferred embodiment, are employed on unicentric hinge 18. Although various flexion and extension stop elements within a hinge can be employed, in the preferred embodiment of knee orthosis 10, those covered by U.S. Pat. No. 6,039,709, and commonly referred to as a KWIK SET™ hinge, are used and is hereby incorporated by reference. The flexion and extension settings are used for setting a range of motion for the knee joint depending on severity of injury or condition pre or post-surgery.

Referring now to FIGS. 1 and 2, it is shown that knee orthosis 10 of the present invention employs a unique system for applying a corrective and therapeutic force to the patient's joint or a lower leg portion below said knee joint or an upper leg portion above said knee joint, or any combination thereof. In particular, a plurality of inflatable air bladders 72 are positioned along inner surfaces of first and second vertical struts 12 and 14. Various attachment mechanisms can be used for securing bladders 72 thereto, however in the preferred embodiment, hook and loop material is employed. Other alternate embodiments (although not shown) provide for air bladders 72 to be embedded within channels of vertical struts 12 and 14. Further, liquid or gel filled bladders can also be employed.

The placement of air bladders 72, and the number to be used, depends on the specific needs of each patient. And as illustrated in FIGS. 1 and 2, four bladders are employed. Two bladders 72 are placed at each hinge, 16 and 18, and two are positioned below hinges 16 and 18 along inner surfaces of bottom portions 22 and 26 of first and second vertical struts 12 and 14, respectively. However, although not shown, another pair of bladders 72 could be employed above hinges 16 and 18, at inner surfaces of top portions 20 and 24 of first and second vertical struts 12 and 14, respectively. Further, any number combination of one to six bladders 72 can be employed with knee orthosis 10 of the present invention.

As further shown in FIGS. 1 and 2, inflation tubes 74 are employed for each air bladder 72, wherein a tip portion 76 is used to inflate or deflate each respective bladder 72. A small bulbous hand pump (not shown) is used to perform the inflation or deflation process.

Referring now to FIGS. 8 and 9, it is shown that hinges 16 and 18 are covered by a soft and pliable wrap 78. In actuality, FIG. 8 illustrates a hinge without a wrap 78, while FIG. 9 illustrates how the wrap 78 covers both the hinge and the air bladder is so employed at the hinge. Wrap 78 employs a material having a high coefficient of friction along a surface that comes into contact with a patient's skin. However, such material is not abrasive to the skin but instead provides has a soft and pleasurable feel and assists in preventing orthosis slippage or migration. In fact, the material employed actually works better to prohibit migration or slippage when it gets wet, which is a very common occurrence with knee orthotics and braces due to body sweat.

Figure 6:
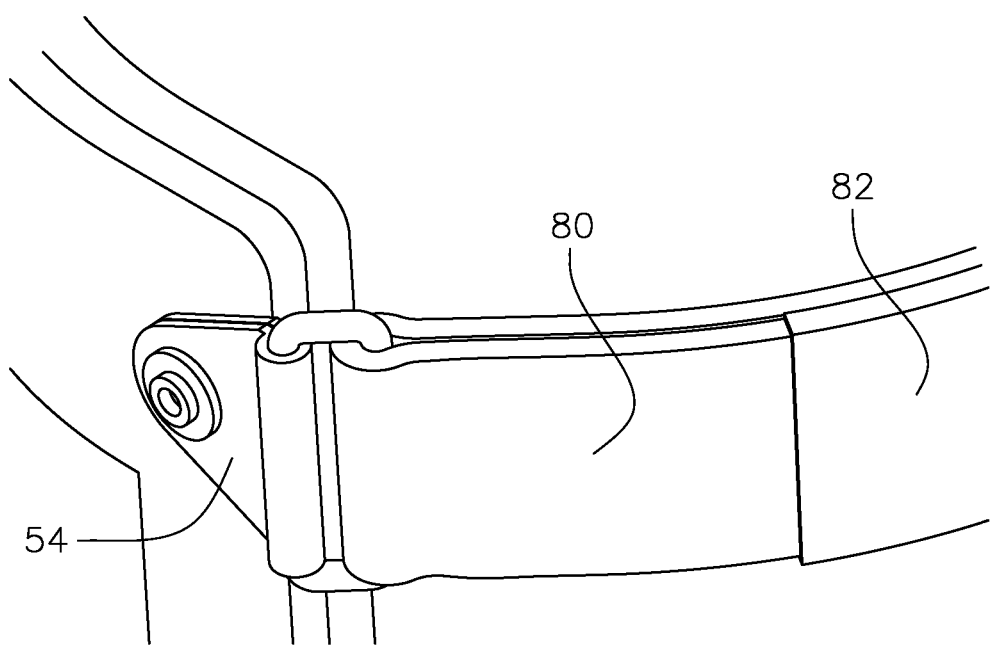
FIG. 6 is a front view of one of a multitude of strap members employed in the novel knee orthosis of the present invention, the strap member in a generally relaxed state.
Figure 7:
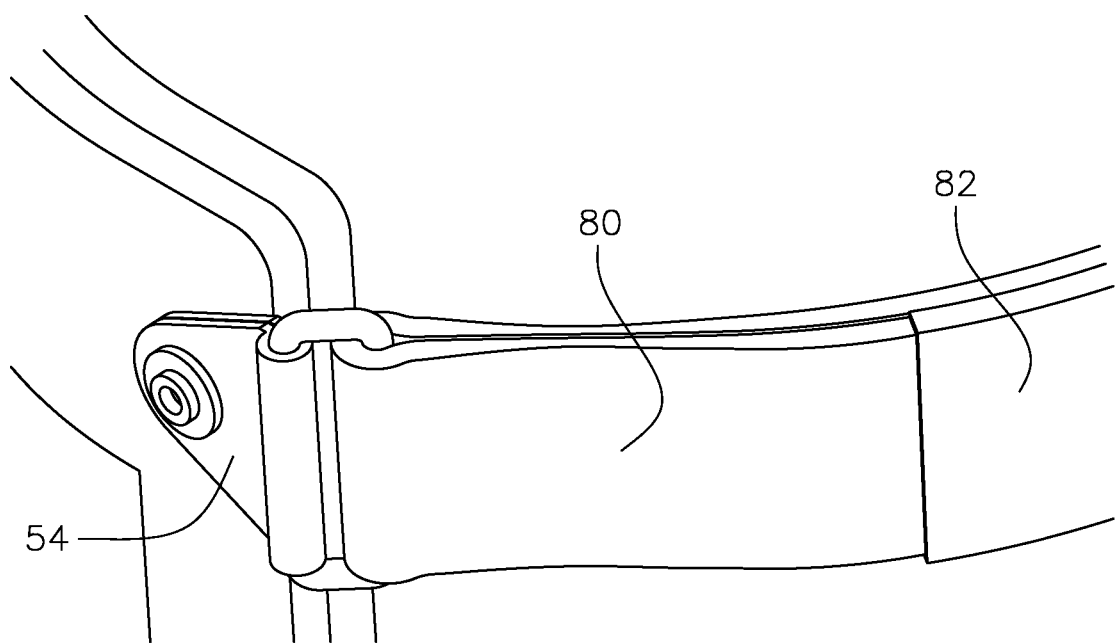
FIG. 7 is a front view of one of the multitude of strap members employed in the novel knee orthosis of the present invention, the strap member in a tensed state due some amount of dimensional change of the a leg muscle group of the patient's leg that is surrounded by said knee orthosis.

Referring now to FIGS. 6 and 7, an end portion 80 (of two opposed ends) of a strap member is shown. Although these two figures represent first thigh strap member 34, the properties and elements to be described directly hereinafter are meant to be apply to, and therefore can be used, with all straps utilized with knee orthosis 10 as previously disclosed above. As shown, opposed end portions 80 of the strap have a greater elasticity than a middle portion 82. This unique feature assists knee orthosis 10 in dynamically conforming in response to any change in dimension of any specific muscle group that is surrounded by knee orthosis 10 when the patient walks, runs, sits, stands up, squats or performs any other necessary ambulatory or athletic motion and/or movement. This all occurs while maintaining total support and stabilization of the knee joint. Further, is it understood that all straps employed in the present invention can be either differentially elastic as described directly hereinabove, equally elastic through the entire strap, static or any combination thereof. Further, various combinations of differentially elastic, totally elastic or static can be employed at different positions about knee orthosis 10 for all of the straps employed herein.

Figure 3:
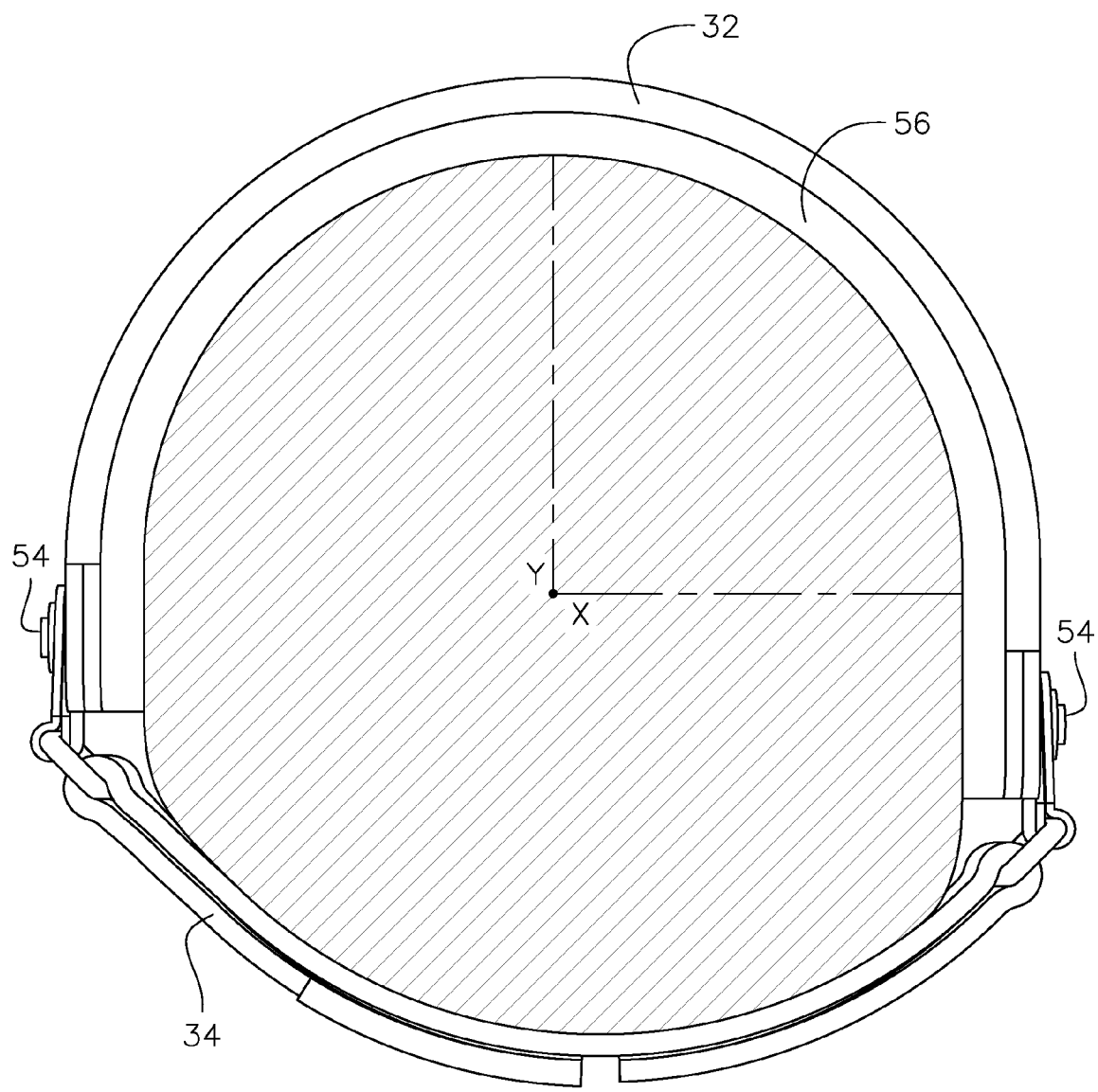
FIG. 3 is a top plan view of the present knee orthosis surrounding a patient's upper leg, the knee orthosis conforming dynamically to a one of a plurality of different dimensional shape changes of said leg due to flexion and elongation thereof.
Figure 4:
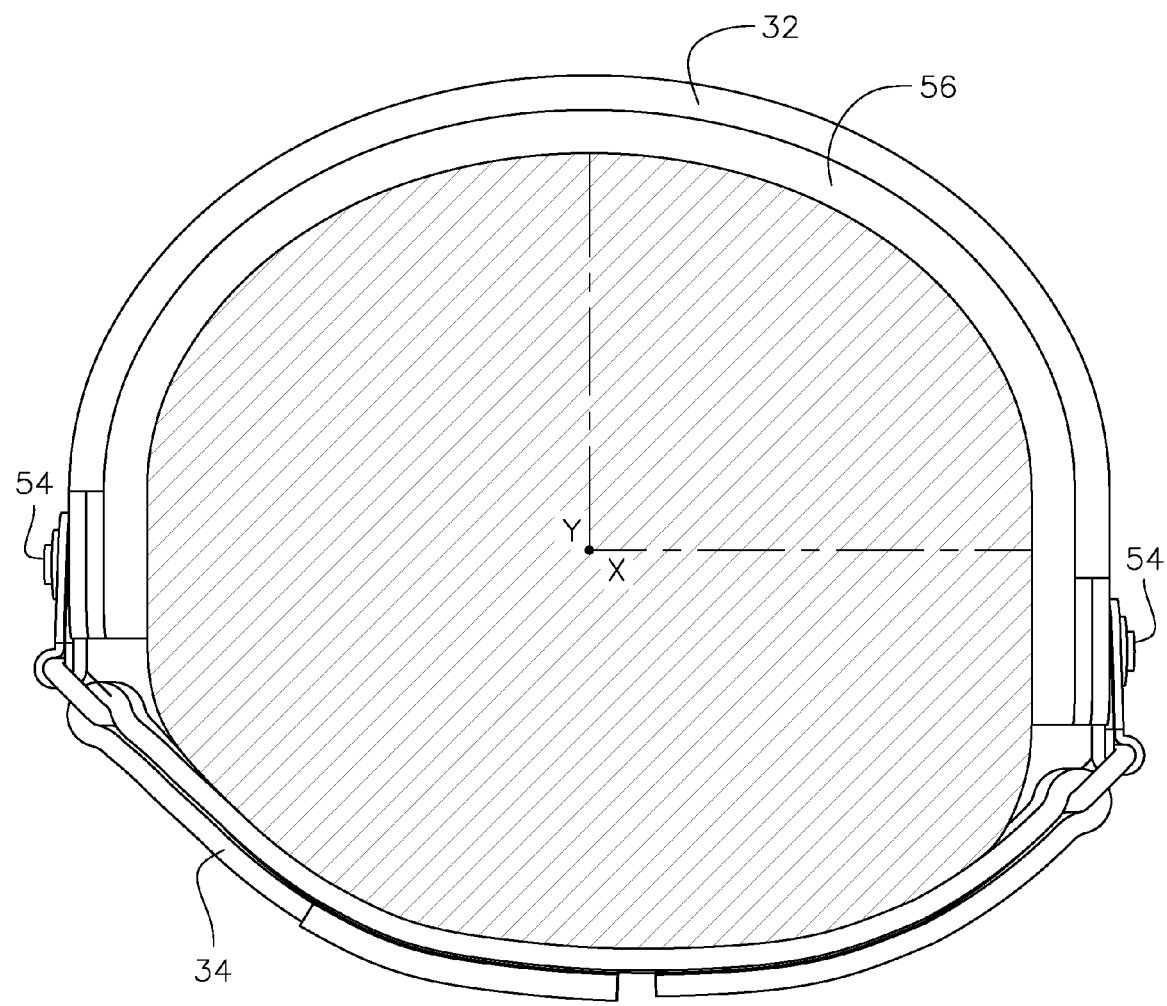
FIG. 4 is a top plan view of the present knee orthosis surrounding the patient's upper leg, the knee orthosis conforming dynamically to a second of a plurality of different dimensional shape changes of said leg due to flexion and elongation thereof.
Figure 5:
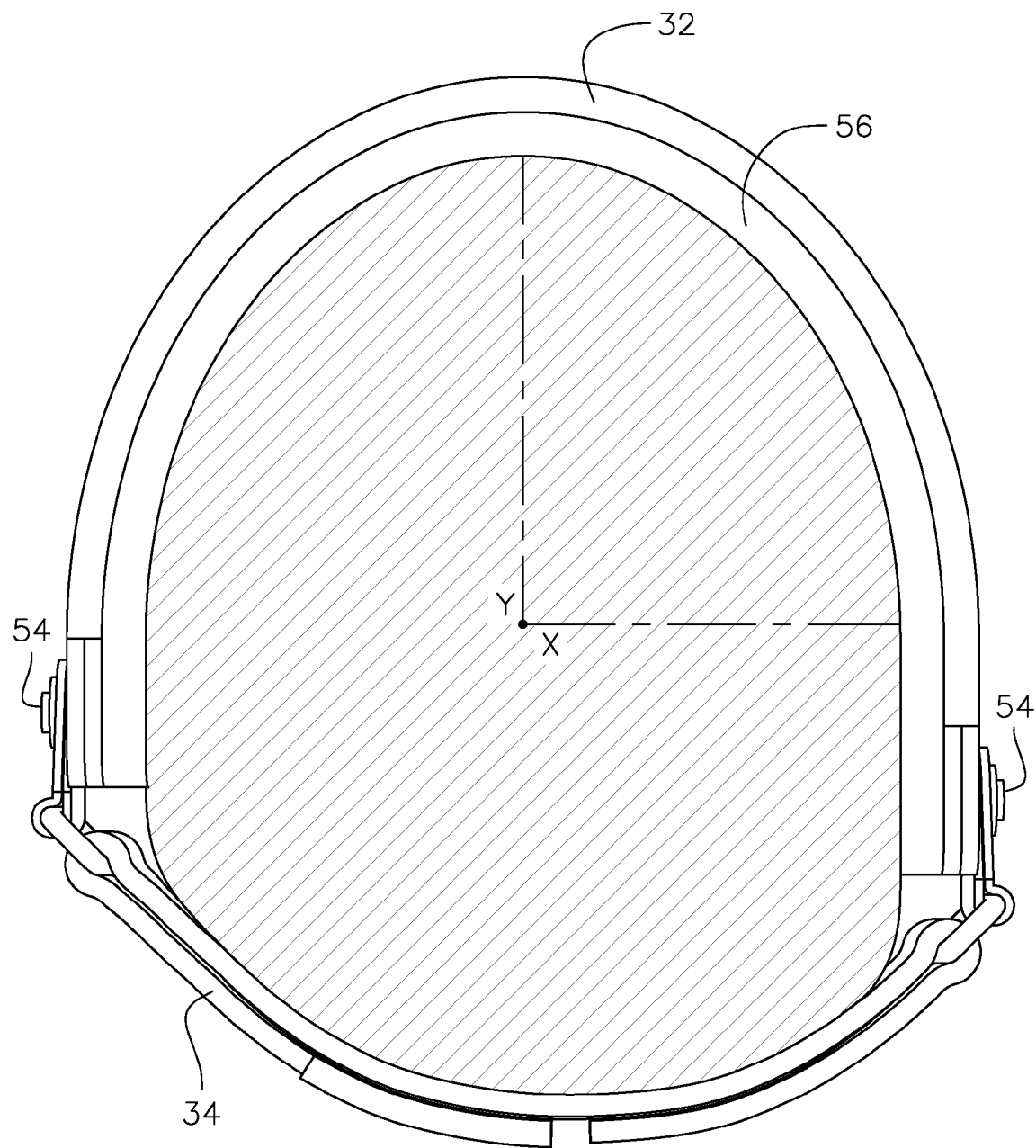
FIG. 5 is a top plan view of the present knee orthosis surrounding the patient's upper leg, the knee orthosis conforming dynamically to a third of a plurality of different dimensional shape changes of said leg due to flexion and elongation thereof.

Referring now to FIGS. 3, 4 and 5, illustrations of just three of a multiplicity of dimensional changes that can occur to the muscle groups that are surrounded by knee orthosis 10 are shown. As illustrated in these three figures, the radius of each X and Y axis is of varying length when measured and compared to one another. Remembering that these are just three of a multiplicity of dimensional changes that can occur to the muscle groups that are surrounded by knee orthosis 10 when ambulatory or athletic motion and/or movement occurs, the Y radial axis of FIG. 5 is greater than the Y radial axis of FIG. 3, which in turn is greater than the Y radial axis of FIG. 4. Likewise, the X radial axis of FIG. 4 is greater than the X radial axis of FIG. 3, which in turn is greater then the X radial axis of FIG. 5.

In providing dynamic conformability to knee orthosis 10, certain materials are used that assist in this unique feature of the present invention. In particular thigh cuff 32 and shin cuff 38 are from a semi-rigid material that provides both some level of flexibility and a level of strength at the same time.

Other equivalent elements can be substituted for the elements disclosed herein to achieve the same results in the same way and in the same manner.

Having thus described the invention, what is claimed for Letters Patent follows:

1. A knee orthosis device for stabilizing and/or immobilizing a knee joint of a patient, the knee orthosis comprising:
   a) at least one vertical strut member having a hinged element intermediately disposed top and bottom portions of the at least one vertical strut member, the hinged element permitting the patient to flex and extend a leg associated with said knee joint;
   b) a semi-rigid, dynamically conformable thigh cuff adapted to be positioned above the knee joint and attached to at least one side thereof to an upper end portion of the at least one vertical strut member top portion, the semi-rigid, dynamically conformable thigh cuff adapted to generally surround a portion of a circumference of a thigh muscle group;
   c) a semi-rigid, dynamically conformable shin cuff adapted to be positioned below the knee joint and attached to at least one side thereof to a lower end portion of the at least one vertical strut member bottom portion, the semi-rigid, dynamically conformable shin cuff adapted to generally surround a portion of a circumference of a shin/calf muscle group;

d) a thigh strapping system including at least one elastic thigh strap member for completing a remaining circumference of the thigh muscle group; e) a shin strapping system including at least one elastic shin strap member for completing a remaining circumference of the shin/calf muscle group;

f) the semi-rigid, dynamically conformable thigh cuff, the thigh strapping system, the semi-rigid, dynamically conformable shin cuff and the shin strapping system all working in coincidence to permit circumferential dimensional change to the knee orthosis during ambulatory or athletic motion of the patient's knee and surrounding muscle groups above and below said knee joint; and g) the at least one elastic thigh strap member and the at least one elastic shin strap member have a higher coefficient of elasticity at opposed end portions thereof as compared to middle portions there between.

2. A knee orthosis device for stabilizing and/or immobilizing a knee joint of a patient, the knee orthosis comprising:

a) at least one vertical strut member having a hinged element intermediately disposed top and bottom portions of the at least one vertical strut member, the hinged element permitting the patient to flex and extend a leg associated with said knee joint;

b) a semi-rigid, dynamically conformable thigh cuff adapted to be positioned above the knee joint and attached to at least one side thereof to an upper end portion of the at least one vertical strut member top portion, the semi-rigid, dynamically conformable thigh cuff adapted to generally surround a portion of a circumference of a thigh muscle group;

c) a semi-rigid, dynamically conformable shin cuff adapted to be positioned below the knee joint and attached to at least one side thereof to a lower end portion of the at least one vertical strut member bottom portion, the semi-rigid, dynamically conformable shin cuff adapted to generally surround a portion of a circumference of a shin/calf muscle group;

d) a thigh strapping system including at least one elastic thigh strap member for completing a remaining circumference of the thigh muscle group;

e) a shin strapping system including at least one elastic shin strap member for completing a remaining circumference of the shin/calf muscle group;

f) the semi-rigid, dynamically conformable thigh cuff, the thigh strapping system, the semi-rigid, dynamically conformable shin cuff and the shin strapping system all working in coincidence to permit circumferential dimensional change to the knee orthosis during ambulatory or athletic motion of the patient's knee and surrounding muscle groups above and below said knee joint; and g) means for providing gait kinetic swing-assistance.

3. The knee orthosis of claim 2, wherein the means for providing gait kinetic swing-assistance is an adjustable dynamic mechanism at the hinged element.

4. The knee orthosis of claim 3, wherein the adjustable dynamic mechanism comprises a system having a means for providing variable tension swing assist forces.

5. The knee orthosis of claim 4, wherein the means for providing variable tension swing assist forces is chosen from the group consisting of a plurality of setting blocks in combination with at least one elastic or spring element, a variably settable cam system and an interchangeable spring element.

6. The knee orthosis of claim 1, wherein the adjustable dynamic mechanism comprises an elastic or spring element positioned over at least one setting block.

7. A dynamically conformable knee orthosis for providing patient knee joint stabilization, the dynamically conformable knee orthosis comprising:

a) a pair of opposed vertical strut members, each strut member having a hinged element intermediately disposed top and bottom portions thereof, the hinged elements permitting the patient to flex and extend a leg associated with said knee joint;

b) a dynamically conformable thigh circumferential band system;

c) a dynamically conformable shin circumferential band system; and d) means for strengthening a patient's leg musculature above the knee joint.

8. The dynamically conformable knee orthosis of claim 7, further comprising means for applying a corrective and therapeutic force to the patient's knee joint and at least to a lower leg portion below said knee joint or to an upper leg portion above said knee joint, or to the patient's knee joint and to the lower and upper leg portions below and above said knee joint.

9. The dynamically conformable knee orthosis of claim 7, wherein the means for strengthening a patient's leg musculature above the knee joint is a dynamic gait kinetic swing-assistance mechanism.

10. The dynamically conformable knee orthosis of claim 9, wherein the dynamic gait kinetic swing-assistance mechanism is chosen from the group consisting of a plurality of setting blocks in combination with at least one elastic or spring element, a variably settable cam system and an interchangeable spring element.

* * * * *